United States Patent [19]

Nugent et al.

[11] Patent Number: 4,804,540
[45] Date of Patent: Feb. 14, 1989

[54] PROCESS FOR PREPARING THE COMBINATION PRODUCTS OF TRIAMTERENE AND HYDROCHLOROTHIAZIDE

[75] Inventors: Frederic J. Nugent, Sherwood Park; John K. C. Yen, Oakville, both of Canada

[73] Assignee: G. D. Searle & Co., Chicago, Ill.

[21] Appl. No.: 133,708

[22] Filed: Dec. 16, 1987

[51] Int. Cl.$^4$ ............................................. A61K 9/52
[52] U.S. Cl. ................................. 424/457; 424/490; 424/489; 424/464; 424/470; 424/469
[58] Field of Search ............... 424/489, 464, 469, 470, 424/457, 490

[56] References Cited

U.S. PATENT DOCUMENTS

| | | | |
|---|---|---|---|
| 2,853,418 | 9/1958 | Smith et al. | 514/271 |
| 3,081,230 | 3/1963 | Weinstock et al. | 514/23.5 |
| 3,184,386 | 5/1965 | Stephenson et al. | 424/471 |
| 4,139,589 | 2/1979 | Beringer et al. | 264/250 |
| 4,165,998 | 8/1979 | Adams et al. | 156/64 |
| 4,168,308 | 9/1979 | Wretlind et al. | 424/244 |
| 4,197,289 | 4/1980 | Sturzenegger et al. | 424/443 |
| 4,248,856 | 2/1981 | Guley et al. | 424/493 |
| 4,248,857 | 2/1981 | DeNeale et al. | 424/493 |
| 4,255,413 | 3/1981 | Rattie et al. | 424/452 |
| 4,285,947 | 8/1981 | Higuchi et al. | 424/251 |
| 4,309,405 | 1/1982 | Guley et al. | 424/493 |
| 4,309,406 | 1/1982 | Guley et al. | 424/489 |
| 4,444,769 | 4/1984 | Blume et al. | 424/470 |
| 4,459,279 | 7/1984 | Stricker et al. | 424/459 |
| 4,526,777 | 7/1985 | Blume et al. | 424/470 |
| 4,547,498 | 10/1985 | Blume et al. | 514/225 |
| 4,681,765 | 7/1987 | Guley | 424/456 |

OTHER PUBLICATIONS

Blume et al. The American Journal of Medicine, 59-61, Nov. 5, 1984.
S. Hah et al. Biopharmaceutics and Drug Disposition, vol. 5, 11-19, 1984.
Randolph et al. Current Therapeutic Research, vol. 38, No. 6, Dec. 1985.
Pruitt et al., Clinical Pharmacology and Therapeutics, vol. 21, No. 5, 610-619.
Marshall, Applied Clinical Pharmacokinetics—233-239, 1983.
Yen, Canadian Pharaceutical Journal, Nov., 1964.
Tannenbaum et al. Clinical Pharmacology and Therapeutics, vol. 9, No. 5, 598-604, 1968.
Dittert et al. Journal of Pharmaceutical Sciences, vol. 53, No. 11, Nov., 1964.
Sorgel et al. Journal of Pharmaceutical Sciences, vol. 75, No. 2, 1986.

*Primary Examiner*—Thurman K. Page
*Assistant Examiner*—L. R. Horne
*Attorney, Agent, or Firm*—Paul D. Matukaitis; Joy Ann Serauskas

[57] ABSTRACT

A combination pharmaceutical composition is described, together with the process for manufacturing said pharmaceutical composition wherein the active ingredients, namely triamterene and hydrochlorothiazide, are incorporated into a solid dosage form via a single wet granulation process utilizing an acid component. Said process simplifies the formulation and manufacturing, permits greater uniformity, and increases in vitro dissolution.

14 Claims, No Drawings

1

PROCESS FOR PREPARING THE COMBINATION PRODUCTS OF TRIAMTERENE AND HYDROCHLOROTHIAZIDE

FIELD OF THE INVENTION

This invention relates to a novel pharmaceutical composition having effective combined diuretic and antihypertensive properties while also being capable of resisting hypokalmeia. This invention provides a formulation for combining active ingredients having significantly different hydrophobic and/or hydrophilic properties. Specifically this invention provides a process formulation for a combination product containing triamterene (2,4,7-triamino-6-phenylpteridine) and hydrochlorothiazide (6-chloro-3,4-dihydro-2H-1,2,4-benzothiadiazide-7-sulfonamide-1,1-dioxide). This invention also provides a process which utilizes an acid component and a solvent for manufacturing the combination product of triamterene and hydrochlorothiazide.

DESCRIPTION OF THE PRIOR ART

Hydrochlorothiazide is a thiazide administered to human patients in order to provide diuretic and antihypertensive medication and treatment. In addition to producing beneficial effects on hypertension, the diuretic action serves to relieve edema caused by renal, cardiac, hepatic ineffectiveness or other causes. However, one of the problems which arises when administering single-entity hydrochlorothiazide is that this medication also tends to cause a loss of potassium from the patient, which may be excessive and which may thereby create an undesired hypokalemia condition. While potassium supplements have been prescribed, this may cause further adverse side effects. Therefore, in order to eliminate the problems associated with the administration of potassium supplements, it is known to administer hydrochlorothiazide in combination with a compound capable of resisting hypokalmeia. Triamterene is a compound capable of resisting hypokalemia. Thus a combination product consisting of hydrochlorothiazide and triamterene is known in the art. Descriptions of such combinations are found in U.S. Pat. No. 3,081,230; "Bioequivalence Study of a New Tablet Formulation of Triamterene and Hydrochlorothiazide" by Blume, et al.; The American Journal of Medicine: Nov. 5, 1984: pp. 59–61 and "The Influence of Dosage Form on the Activity of a Diuretic Agent" by Tannenbaum, et al. Clinical Pharmacology and Therapeutics, Volume 9, No. 5, pp. 598–604 (1968).

However, triamterene's relative hydrophobic characteristics adversely affect the relatively hydrophilic hydrochlorothiazide resulting in a decrease in the dissolution rate in physiological fluids of both active ingredients and thus, their bioavailabilities. Because of this attempts to combine these active ingredients have not been without problems. Descriptions of combinations of triamterene and hydrochlorothiazide as well as methods for their formulation are known from U.S. Pat. Nos. 4,444,769, 4,526,777 and 4,547,498 and references cited therein.

U.S. Pat. No. 4,444,769 describes a method of administering a solid antihypertensive diuretic medication by orally administering a composition composed of (1) finely divided particles of a benzothiadiazide ingredient which has been first separately mixed with at least one finely divided pharmaceutically acceptable ingredient and (2) finely divided particles of a pteridine ingredient which has been first separately mixed with at least one finely divided pharmaceutically acceptable ingredient as well as a non-toxic pharmaceutically acceptable carrier material such as wicking agent, surfactant, disintegrant, lubricant, or compacting aid. The relatively hydrophobic pteridine ingredient particles are substantially isolated from direct contact with the benzothiadiazide ingredient particles in the composition. The "769" patent further describes a granularly-heterogeneous composition having combined pharmaceutically effective antihypertensive diuretic and antihypokalemic properties composed of discrete, separately formed first granules containing finely divided particles of a triameterene active pteridine ingredient mixed with at least one finely divided pharmaceutically acceptable inert ingredient and separately formed second granules containing a hydrochlorothiazide active benzothiadiazide ingredient mixed with at least one finely divided pharmaceutically active ingredient. The first and second granules are mixed and blended together so that the resulting blended composition has a weight ratio of the pteridine ingredient to the benzothiadiazide ingredient which provides an effective bioavailability of the pteridine to control the hypokalemic condition induced by the dosage amount of the benzothiadiazide.

U.S. Pat. No. 4,526,777 which is a divisional of U.S. Pat. No. 4,444,769 described a method for enhancing the bioavailability of pharmaceutical combination compositions in solid unit dosage form which are composed of at least two solid pharmaceutically active ingredients of respectively different hydrophilic characteristics, at least one of which is sparingly soluble in physiological fluids. The method consists essentially in (1) separately providing each of said active ingredients in finely divided particulate solid form; (2) separately mixing each of said finely divided active ingredients with respective non-toxic pharmaceutically acceptable inert carrier materials in finely divided particulate form; (3) separately compacting the respective active ingredients with their respective carrier materials to form separate compactions thereof; (4) thereafter separately comminuting said separate compactions to form respectively separate granules of the respective active ingredients; and (5) thereafter mechanically blending the respective granules together in the desired optimum pharmaceutically effective proportions to form a granularly heterogeneous blended combination whereby the respective active ingredients' particles are substantially retained within the respective granules and then forming the blended composition into unit dosage entities.

The "777" patent further describes a pharmaceutical combination composition having at least first and second pharmaceutically active ingredients, at least one of which ingredients is sparingly soluble in an aqueous physiological fluid and which ingredients are of different hydrophobic or hydrophilic characteristics. The composition is composed of a granularly-heterogeneous but substantially homogeneous blend of said ingredients with the respective first and second ingredients being present in finely divided particulate form and having been first separately compacted and then separately comminuted into respectively separate granules, whereby one set of granules contains substantially only the first active ingredient in admixture with a first set of nontoxic pharmaceutically acceptable inert carrier materials and the second set of granules contains the second active ingredient in separate admixture with a second set of nontoxic pharmaceutically acceptable inert carrier materials. The carrier materials are compatible with the active ingredients and functionally capable of aiding disintegration of the respective granules and dissolution of the respective ingredients upon exposure to physiological fluid. The composition exhibits enhanced bioavailability of at least one of the ingredients relative to the bioavailability of that ingredient in a combination of homogeneous granules containing both of the respective finely divided ingredient particles in intimate admixture with each other.

U.S. Pat. No. 4,547,498 which is also a division of a U.S. Pat. No. 4,444,769 describes a method for forming a granularly-heterogeneous composition having combined pharmaceutically acceptable diuretic, antihypokalemic, and anithypertensive activity comprising the steps of (1) first mixing finely divided particles of a triameterene active pteridine ingredient with at least one finely divided pharmaceutically acceptable inert ingredient to form a first mixture and granulating this first mixture to form first granules, then (2) separately mixing finely divided particles of a hydrochlorothiazide active benzothiadiazide ingredient with at least one finely divided pharmaceutically acceptable inert ingredient to form a second mixture and separately granulating the second mixture to form second granules. The first granules and second granules are then physically blended together while substantially retaining the respective identifies of the first and second granules in respective amounts such that in the resulting blended composition the weight ratio of the pteridine ingredient to the benzothiadiazide ingredient provides an effective bioavailable amount of pteridine to control the hypokalemic condition induced by the dosage amount of the benzothiadiazide.

The present invention differs from the prior art (U.S. Pat. No. 4,444,769) in that it is a simple one step wet granulation process (see Chart A) rather than two separate compaction processes (see Chart B) for the combination product of triamterene and hydrochlorothiazide. In the process of the present invention the triamterene and hydrocholorothiazide are mixed together with certain pharmaceutically acceptable inert ingredients and then the mixture of these two active ingredients with other inert ingredients is processed into the final form of the composition. The prior art process requires the mixing of the active ingredients separately with inert pharmaceutically acceptable carriers prior to mixing the two active ingredients together. Additionally the process of the present invention utilizes an acid component in the presence of a solvent. No such acid component in the prsence of a solvent is taught in the prior art. Components such as wetting agents or surfactants or flow enhancers are not necessary in the present invention.

CHART A

| PROCESS OF THE PRESENT INVENTION | |
|---|---|
| Triamterene | Hydrochlorothiazide |
| ( 95% passes through 100 mesh | 95% passes through 100 mesh ) |
| Wicking | |
| Binder/Disintegration Agent | |
| Blending | |
| Milling | |
| Granulation | |
| Solvent, Acid and Binder | |
| Drying | |
| Milling | |
| Disintegrant | |
| Lubricant | |

CHART A-continued

| PROCESS OF THE PRESENT INVENTION | |
|---|---|
| Triamterene | Hydrochlorothiazide |
| Blending | |
| Compression or Encapsulation | |

CHART B

| PRIOR ART PROCESS | |
|---|---|
| Triamterene | Hydrochlorothiazide |
| Milling | Milling |
| 95% Passes through | 95% Passes through |
| 200 mesh | 100 mesh |
| Wicking Agent | Binder/Disintegrant |
| Binder/Disintegrant | Carrier/Disintegrant |
| Wetting Agent | Flow Enhancer |
| Carrier/Disintegrant | Lubricant |
| Lubricant | |
| Flow Enchancer | |
| Blending | Blending |
| Milling | Milling |
| Compaction | Compaction |
| Milling | Milling |
| Lubricant | |
| Blending | |
| Compression or Encapsulation | |

GENERAL SUMMARY OF THE INVENTION

The present invention provides a pharmaceutical composition containing both triamterene and hydrochlorothiazide in a solid dosage form having properties of increased in vitro dissolution. The resulting in vivo bioavailability thereby permitting effective diuretic and antihypertensive activity while resisting the undesirable side effect of hypokalmeia.

An object of the invention is to provide a pharmaceutical composition combining triamterene and hydrochlorothiazide in which said pharmaceutical composition provides effective diuretic and antihypertensive activity while resisting the undesirable side effect of hypokalemia.

Another object of the invention is to provide a process for manufacturing a pharmaceutical composition wherein said pharmaceutical composition is composed of two active ingredients, one active ingredient having hydrophobic characteristics and the other having hydrophilic characteristics.

A further specific object of the invention is to provide a process for manufacturing a pharmaceutical composition wherein said pharmaceutical composition is composed of triamterene and hydrochlorothiazide and wherein the resulting pharmaceutical composition has increased bioavailability with resulting increased therapeutic efficacy of the combination product of triamterene and hydrochlorothiazide.

Another specific object of the present invention is to provide a simple formulation for a combination product of triamterene and hydrochlorothiazide.

DESCRIPTION OF THE PREFERRED EMBODIMENTS

In a preferred embodiment of the present invention triamterene and hydrochlorothiazide are combined along with suitable non-toxic pharamaceutical carriers to produce the desired pharmaceutical action.

A preferred embodiment for the method of manufacturing the pharmaceutical composition of the present invention comprises the steps of providing respective quantities of triamterene and hydrochlorothiazide at a weight ratio of triamterene to hydrochlorothiazide of about 2.00 to 1.25:1. The active ingredients (triamterene and hydrochlorothiazide) are mixed together with a wicking binding, disintegration agent and then blended, milled and granulated with solvent and acid. This is followed by further milling, drying, mixing with a disintegrant and lubricant, and final blending. The final dosage form may be a tablet by compression or capsule by encapsulation.

The quantity of triamterene on w eight basis should bein the range of about 2.00 to 1.25 times the quantity of hydrochlorothiazide, preferably about 1.5:1. The expression "triamterene weight base" shall refer to the ratio of the amount on a weight basis of another component to the amount of triamterene.

The active ingredient triamterene, in a milled form, preferably having a particle size specification of not less than 95% through a 100 mesh screen; the active ingredient hydrochlorothiazide, in a milled form, preferably having a particle size specification of not less than 95% through a 100 mesh screen and a suitable wicking, binding, disintegration agent such as microcrystalline cellulose, N.F. $(C_6H_{10}O_5)_n$ are blended into a mixture. The ratio of triamterene to hydrochlorothiazide is a ratio of 2.00 to 1.25:1 with a ratio of 1.5:1 being preferred. The amount of microcrystalline cellulose which functions as a wicking, binding and disintegration agent is that amount which would produce effective dissolution of the active ingredients. A preferred range of microcrystalline cellulose is about 50 to 750 percent (on a triamterene weight basis) and preferably about 150 to 400 percent. Microcrystalline cellulose is a preferred wicking, binding and disintegration agent; however, other wicking, binding and disintegration agents which are capable of producing effect dissolution of the actives would also be suitable for the practice of this invention.

The resultant mixture is now milled. The milling procedure is preferably accomplished by the passing of the mixture through a mill, such as a Comil ® fitted with a 032R screen with an impeller speed of 1000 rpm. The milled mixture should be free of any undispersed aggregate of active ingredients and uniformed. Said mixture is now transferred to mixing/granulation type of equipment. It is the purpose of this milling to produce a mixture which is free of any undispersed aggregates of active ingredients. Thus it is understood that other commercially available mills fitted with various size screens and run at different impeller speeds would also be suitable for the practice of this invention, provided that the above-defined purpose is accomplished by the equipment.

A granulation liquid is prepared by dispersing/dissolving a binder such as povidone (polyvinylpyrrolidone) of about 10 to 70 percent on a triamterene weight basis and preferably about 20 to 35 percent and an acid component such as malic acid of about 5 to 45 percent on a triamterene weight basis and preferably about 10 to 25 in a solvent such as purified water of about 50 to 650 percent on a triamterene weight basis and preferably about 150 to 260. While povidone is a preferred binder, other agents which are capable of imparting cohesive qualities to powdered material may also be suitable for the practice of this invention.

The above-described granulation liquid was slowly added to the milled powder with continuous mixing to form a soft, wet mass. The mixing time should be about 1 to 30 minutes and preferably about 3-15 minutes. The wet mass was then milled through a mill such as a Comil ® fitted with a 250R screen at an impeller speed of 725 rpm to permit coarse sizing of the mass into what is commonly referred to as granules. It is the purpose of this milling to permit coarse sizing of the wet mass into granules. Thus it is understood that other commercially available mills fitted with various size screens and run at different impeller speeds would also be suitable for the practice of this invention provided that the above-defined purpose is accomplished by the equipment.

The wet granules were dried in a suitable piece of equipment such as a forced air tray dryer at a temperature range of ambient to 80° C. with 60° C. being preferred. The granules were kept under these conditions for a period of time necessary to obtain residual moisture levels between ½ and 1½%. Thus it is understood that other commercially available dryers would also be suitable for the practice of this invention provided that the above identified purpose is accomplished by the equipment.

Using sieving equipment the dried granules were sized into oversized and undersized granules. The oversized granules were blended with a disintegrant and a lubricant. A disintegrant suitable for the practice of the invention is croscarmellose sodium, N.F. (a cross-linked sodium carobyxmethyl cellulose material), in quantities of about 25 to 125 percent on a triamterene weight basis and preferably about 40 to 60 percent. A lubricant suitable for the practice of the invention is magnesium stearate in quantities of about 0.5 to 10 percent on a triamterene weight basis and preferably about2 and 4 percent. The mixture of the oversized granules, disintegrant and lubricant is milled through a suitable piece of equipment such as a Comil ® fitted with a 062R screen and impeller speed of 725 rpm. This milling reduces the particle size of the large granules to facilitate more uniform distribution during finished dosage form preparation.

It is the purpose of this milling to reduce the particle size of the large granules. Thus it is understood that other commecially available mills fitted with various size screens and run at different impeller speeds would also be suitable for the practice of this invention provided that the above-defined purpose is accomplished by the equipment.

The milled oversized mixture and the undersized granules were mixed in a suitable piece of equipment such as a twin shell blender for a period of time such as three minutes or until there is distribution of the lubricant and disintegrant throughout all granules. The granular mixture is then ready for final dosage form preparation on equipment such as a tablet press or capsule filling machine. Thus it is understood that other commecially available blenders would also be suitable for the practice of this invention provided that the above-identified purpose is accomplished by the equipment.

It will be understood that the same technology which has been described above may be followed with alternative active ingredients. Thus in place of triamterene other pteridine-structurally related compounds have triamterene activity may be used. Further, in place of hydrochlorothiazide other benzothiadiazine-structurally related compounds having hydrochlorothiazide activity may be used. It will be further understood that in a broader aspect the technology which has been described may also be followed for combining active ingredients wherein one active ingredient is relatively hydrophobic in character and the other active ingredient is relatively hydrophilic in character.

The problems of incorporating hydrochlorothiazide and triamterene in a solid dosage form have been recognized as triamterene relative hydrophobic characteristic and its adverse effects on the relatively hydrophilic hydrochlorothiazide. The final result is a decrease in the dissolution rate in physiological fluids of both drug actives and consequently the bioavailability. The problem of controlling the dissolution rate of a drug can be addressed in one of two ways (1) changes in drug solubility or (2) changes in the drug surface area. The prior art of Blume and Bomer has addressed the problem by changing the drug surface area of the drugs thereby reducing the contact surface area between the two actives. The present invention has addressed the problem by changing the triamterene solubility thus making it less hydrophobic. This alteration in triamterene solubility minimizes its adverse effects on the hydrophilic hydrochlorothiazide.

For the combination products of triamterene and hydrochlorothiazide the triamterene dissolution process was found to be the rate-controlling factor in both the disintegration of the tablet into granules and the dissolution of both drugs. Consequently the present invention is based on those factors which affect primarily the solubility term rather than the drug surface area for the triamterene. In the present invention, changing the solubility properties of triamterene caused the dissolution of hydrochlorothiazide to become an independently controlled process from triamterene dissolution. Subsequently, increasing the drug surface area of hydrochlorothiazide was sufficient to increase its dissolution rate.

The present invention possesses two primary features which improve the solubility of triamterene resulting in the combination of triamterene and hydrochlorothiazide having increased in vitro dissolution the acid component and the solvent. The acid component must be present in order to form an acid-triamterene interaction. The solvent must be present to allow this interaction to occur.

The acid used in the practice of this invention can be selected from acids either from organic or mineral origins (in very dilute forms) which are capable of forming an acid-triamterene interaction and are nontoxic when taken internally. Malic acid is the preferred acid. It should also be appreciated that other acids such as citric, tartaric, fumaric, acetic, aminoacetic, lactic, and hydrocloric, would also be suitable for the practice of this invention. While a single acid is preferred, it should also be appreciated that various ratios of acid entities could be used. It is normally appropriate in tablets, capsules and granules to use acid:trimaterene ratios such that the amount of acid to triamterene preferred is between 0.10 and 0.25.

The solvent used in the present invention can be a non-toxic liquid which allows an acid-trimaterene interaction to form. Water is the preferred solvent. However it should also be appreciated that solvents such as ethanol and isopropyl alcohol would also be suitable. The amount of the solvent used will depend upon the amount of evaporation during processing, the amount of acid, the intensity of agitation and the scale of operation. As an example of the amount of solvent, it is normally appropriate in tablets, capsules and granules to use solvent; tiamterene ratios such that the amount of solvent to triamterene preferred is between 1.50 and 2.60. Generally, the amount of solvent will have a range such that the amount used will ensure an acid-triamterene interaction does form.

A secondary feature of the present invention is the mixing time at the point in the process where the granulation liquid is added to the milled powder to form a wet mass. This time feature will be dependent on the acid selected and the solvent as well as the quantities of each.

The invention is more fully described in the following examples. The exmaples are not intended to limit the invention in spirit or scope.

EXAMPLE 1

The combination product of traimtereme (TRM) and hydrochlorothiazide (HCT) with ratio of 1.5 to 1 on a weight basis was prepared using the present technology. The material and amounts are listed in Table 1.

TABLE 1

| Ingredient | mg per Tablet | kg per Lot | % |
|---|---|---|---|
| Triamterene | 75.0 | 1.275 | 25.0 |
| Hydrochlorothiazide | 50.0 | .850 | 16.7 |
| Microcrystalline Cellulose | 120.0 | 2.040 | 40.0 |
| Malic Acid | 10.0 | .170 | 3.3 |
| Povidone | 15.0 | .255 | 5.0 |
| Crosscarmelose Sodium | 28.5 | .485 | 9.5 |
| Magnesium Stearate | 1.5 | .026 | 0.5 |
| Water* | (117.0) | (1.989) | |
| TOTAL | 300.0 mg | 5.100 | 100.0 |

*Removed during drying

In a typical practice of the present invention the TRM, HCT and a suitable binder-disintegrant agent such as microcrystalline cellulose were blended into a mixture. The mixture should be relatively uniform prior to milling. Passing the mixture through a mill, such as Comil ® fitted with an 032R screen with an impeller speed oof 1000 rpm, dispersed aggregates of actives. The milled mixture was transferred to a suitable mixing/granulation type of equipment such as a Hobart ® planetary mixer, speed 43 rpm.

A granulation liquid was prepared by dispersing/dissolving a binder such as providone and an acid component such as malic acid, in a solvent such as water, suing a suitable mixer like an overhead mixer with impeller. The granulation liquid was slowly added to the milled powder with continuous mixing for 5 to 10 minutes to form a soft, wet mass. The wet mass was milled through Comil ® mill fitted with a 250R screen and an impeller speed of 725 rpm to permit coarse sizing of the mass into what is commonly referred to as granules.

The wet granules were dried in a forced air tray dryer at 60° C. The granules were kept under these conditions for a period of time such as 8 hours unitl the residual moisture is between $\frac{1}{2}$ and $1\frac{1}{2}$%. (Residual moisture specifications will change according to the type of analytical equipment used.)

The dried granules were sized through a sieve such as 20 mesh into oversized and undersized granules. The oversized granules were blended with crosscarmelose sodium and magnesium stearate. The mixture of oversized granules, disintegrant and lubricant was milled through a Comil ® mill fitted with an 062R screen and impeller speed of 725 rpm. This milling reduced the particle size of the large granules to facilitate more uniform distribution during the finished dosage form preparation.

The milled oversized mixture and the undersized granules were then mixed in a suitable piece of equipment such as a twin shell blender for a period of time such as three minutes or until there is distribution of the lubricant and disintegrant throughout all granules. The granular mixture is then ready for final dosage form preparation on equipment such as a tablet press (tablet weight of 300 mg and tablet hardness of 7 to 9 kg).

EXAMPLE 2

The present invention was expected to accommodate a range of TRM to HCT ratios. The following table shows selected ratios tested using the procedure of Example 1.

TABLE 2

| TIME | % DISSOLVED | | | |
|---|---|---|---|---|
| | 1.5:1 | | 2.0:1 | |
| (min) | TRM | HCT | TRM | HCT |
| 30 | 96.3 | 95.8 | 92.4 | 86.5 |
| 60 | 101.5 | 97.3 | 97.4 | 94.5 |

EXAMPLE 3

A series of experiments comparing the present invention to the previous method of Blume and Bonner were conducted. In particular, relative standrad deviation (RSD) for the dissolution of the finished product was chosen for comparison. From the results in Table 3 the present invention demonstrated significant improvements over the prior art.

TABLE 3

| | % DISSOLVED | | | |
|---|---|---|---|---|
| TIME | PRIOR ART | | PRESENT INVENTION | |
| (min) | TRM | HCT | TRM | HCT |
| 15 (x of 6) | 82.0 | 97.6 | 87.1 | 90.7 |
| (RSD) | 1.4 | 7.3 | 2.2 | 2.3 |
| 30 (x of 6) | 88.0 | 100.0 | 92.8 | 93.4 |
| (RSD) | 2.4 | 3.9 | 1.1 | 2.0 |
| 45 (x of 6) | 89.6 | 100.3 | 94.7 | 94.7 |
| (RSD) | 3.6 | 3.6 | 1.1 | 1.3 |
| 60 (x of 6) | 91.2 | 99.7 | 94.2 | 94.3 |
| (RSD) | 2.3 | 5.0 | 1.6 | 1.3 |

Upon examination of RSD figures in Table 3, all values, except TRM (at 15 minutes) for the present invention, were smaller in magnitude than those of the prior art. It is evident that the present technology demonstrated significant improvements in the uniform dissolution control of the combination product of TRM and HCT.

EXAMPLE 4

The bioavailability of tablets containing 50 mg hydrochlorothiazide and 75 mg triamterene manufactured by Searle (S) was compared to a currently marketed preparation, Maxzide (M). Thirty-five healthy non-smoking male volunteers participated in this open labeled, single dose, two period, four sequence, randomized, crossover study. Pre and post study evaluation included history, physical exam, ECG, hematology, biochemistry, and urinalysis. All subjects completed both periods of the study. No subject experienced any severe adverse events, and none of the events required that the subject leave the study or other action be taken.

Triamterene (TRM) and the active metabolite (TRM-O-SO$_4$) plasma was measured in 15 samples drawn during the 48 hours after each dose. Urine hydrochlorothiazide (HCT) excretion was measured over 10 collection periods up to 36 hours after the dose. The results are presented in Tables 4, 5, 6, 7 and 8.

Measures of bioavailability for TRM and TRM-O-SO$_4$ were calculated for each subject including:

Peak plasma concentration, highest value reported, $C_{max}$;

Time of peak plasma concentration, $T_{max}$;

Area under the plasma concentration-time curve using the trapezoidal rule during the 48 hour sampling interval, AUC; and Elimination rate constant from the least squares linear regression of the terminal portion of the plasma, concentration time curve (t=4 to 48), Beta Half-life, T-half=0.693/Beta.

Measures of bioavailability for HCT were calculated for each subject including:

Urinary excretion rate for each collection time interval, R;

Peak excretion rate, $R_{max}$;

Time to peak excretion rate, $T_{max}$;

Cumulative excretion at the end of each sampling interval, $E_1 \ldots E_{36}$; including Overall cumulative excretion, $E_{36}$;

Elimination rate constant from the least squares linear regression of the terminal portion of the urine elimination rate time curve (t=6-8 to t=24-36), Beta, Half-life, T-half=0.693/Beta.

Time for the rate, R, was taken as the midpoint at the collection interval;

Plasma TRM and TRM-O-SO$_2$ $C_{max}$; urine $R_{max}$; and $T_{max}$, AUC beta and half-life for both plasma and urine were compared. The results are presented in Table 8.

No significant differences (p<0.05) were noted for TRM at any sampling time after 40 minutes and for each pharmacokinetic parameter (Table 4). AUC and $C_{max}$ for S were approximately 20% higher than M. AUC and $C_{max}$ confidence intervals were outside ±20% (Table 8).

Differences between M and S mean values were appreciably less for TRM-O-SO$_4$. AUC and $C_{max}$ for S were about 12% higher than M. The 90% confidence interval for AUC was within ±20% and $C_{max}$ was within ±25% (Table 8).

No significant differences at any time point were noted for HCT elimination rate (Table 6) or cumulative elimination data. (Table 7) Mean cumulative elimination time points for S were all within 7% for M except at one hour. Mean HCT ratios for AUC, $R_{max}$, $T_{max\ 1\ and\ 36}$ hour cumulative elimination were all within 4% with 90% confidence intervals between ±16% (Table 8).

These results provide sufficient evidence to conclude that TRM-O-SO$_4$ and HCT, the principal active ingredients present after S administration, are bioequivalent to that provided by M. The difference in TRM observed would not be expected to be clinically significant. Thus, the two formulations can be considered bioequivalent to each other.

TABLE 4

PLASMA TRIAMTERENE CONCENTRATION BY TIME
(ng/ml after single 75 mg oral dose)

| Sample Time | Formulation S | Formulation M | Diff (S − M) Mean | St Dev | 90% CI | | 95% CI | | S % | 90% Ratio CI | | 95% Ratio CI | |
|---|---|---|---|---|---|---|---|---|---|---|---|---|---|
| 20 min | 58.71 | 30.18 | 28.52 | 7.68 | 15.66 | 41.39~ | 13.13 | 43.92* | 194.5 | 151.9 | 237.1~ | 143.5 | 245.5* |
| 40 min | 133.21 | 101.12 | 31.08 | 13.64 | 8.22 | 53.95~ | 3.73 | 58.44* | 130.4 | 108.0 | 152.8~ | 103.6 | 157.2* |
| 1 hr | 124.88 | 107.71 | 17.17 | 13.51 | −5.51 | 39.86 | −9.99 | 44.34 | 115.9 | 94.9 | 137.0 | 90.7 | 141.2 |
| 1.5 hrs | 114.12 | 96.05 | 18.07 | 11.02 | −0.42 | 36.55 | −4.06 | 40.20 | 118.8 | 99.6 | 138.1 | 95.8 | 141.8 |
| 2 hrs | 96.61 | 80.36 | 16.25 | 9.61 | 0.13 | 32.36~ | −3.04 | 35.53 | 120.2 | 100.2 | 140.3~ | 96.2 | 144.2 |
| 2.5 hrs | 79.47 | 65.75 | 13.72 | 8.34 | −0.26 | 27.70 | −3.01 | 30.45 | 120.9 | 99.6 | 142.1 | 95.4 | 146.3 |
| 3 hrs | 65.15 | 54.75 | 10.41 | 7.01 | −1.33 | 22.14 | −3.64 | 24.46 | 119.0 | 97.6 | 140.5 | 93.4 | 144.7 |
| 4 hrs | 45.15 | 37.91 | 7.24 | 4.90 | −0.98 | 15.47 | −2.60 | 17.09 | 119.1 | 97.4 | 140.8 | 93.2 | 145.1 |
| 6 hrs | 19.11 | 16.44 | 2.67 | 2.11 | −0.87 | 6.22 | −1.57 | 6.92 | 116.3 | 94.7 | 137.8 | 90.4 | 142.1 |
| 8 hrs | 10.36 | 8.28 | 2.08 | 1.19 | 0.08 | 4.07~ | −0.32 | 4.47 | 125.1 | 100.9 | 149.2~ | 96.1 | 154.0 |
| 12 hrs | 3.38 | 3.20 | 0.18 | 0.67 | −0.94 | 1.31 | −1.17 | 1.53 | 105.7 | 70.5 | 140.9 | 63.6 | 147.8 |
| 24 hrs | 0.31 | 0.55 | −0.24 | 0.30 | −0.76 | 0.28 | −0.86 | 0.39 | 56.9 | −38.3 | 152.0 | −57.7 | 171.4 |
| 36 hrs | 0.13 | 0.06 | 0.08 | 0.15 | −0.19 | 0.34 | −0.25 | 0.40 | 228.6 | −224.0 | 681.1 | −327.0 | 783.9 |
| 48 hrs | 0.09 | 0.06 | 0.03 | 0.10 | −0.16 | 0.21 | −0.20 | 0.25 | 147.6 | −167.0 | 461.9 | −234.0 | 529.7 |

S = Searle tablets containing 50 mg hydrochlorothiazide and 75 mg triamterene
M = Maxzide tablets containing 50 mg hydrochlorothiazide and 75 mg triamterene
S % = 100% × S/M
CI = Confidence interval including the preceding mean
~Statistically different at p < 0.1 level.
*Statistically different at p < 0.05 level.

TABLE 5

PLASMA TRM-O—SO₄ CONCENTRATION BY TIME
(ng/ml after single 75 mg oral dose)

| Sample Time | Formulation S | Formulation M | Diff (S − M) Mean | St Dev | 90% CI | | 95% CI | | S % | 90% Ratio CI | | 95% Ratio CI | |
|---|---|---|---|---|---|---|---|---|---|---|---|---|---|
| 20 min | 224.36 | 118.67 | 105.69 | 33.38 | 49.38 | 162.01~ | 38.18 | 173.21* | 189.1 | 141.6 | 236.5~ | 132.2 | 246.0* |
| 40 min | 1004.06 | 770.70 | 233.36 | 87.19 | 85.57 | 381.14~ | 55.90 | 410.81* | 130.3 | 111.1 | 149.5~ | 107.3 | 153.3* |
| 1 hr | 1170.53 | 1058.55 | 111.98 | 87.42 | −34.67 | 258.64 | −63.55 | 287.51 | 110.6 | 96.7 | 124.4 | 94.0 | 127.2 |
| 1.5 hrs | 998.77 | 949.59 | 49.18 | 65.48 | −60.57 | 158.94 | −82.15 | 180.52 | 105.2 | 93.6 | 116.7 | 91.3 | 119.0 |
| 2 hrs | 818.37 | 731.19 | 87.18 | 49.82 | 3.69 | 170.66~ | −12.71 | 187.06 | 111.9 | 100.5 | 123.3~ | 98.3 | 125.6 |
| 2.5 hrs | 629.93 | 557.04 | 72.89 | 44.34 | −1.52 | 147.30 | −16.18 | 161.96 | 113.1 | 99.7 | 126.4 | 97.1 | 129.1 |
| 3 hrs | 498.87 | 435.31 | 63.56 | 42.31 | −7.87 | 134.99 | −22.10 | 149.22 | 114.6 | 98.2 | 131.0 | 94.9 | 134.3 |
| 4 hrs | 300.46 | 267.12 | 33.34 | 27.17 | −12.47 | 79.14 | −21.57 | 88.24 | 112.5 | 95.3 | 129.6 | 91.9 | 133.0 |
| 6 hrs | 147.14 | 133.49 | 13.66 | 13.16 | −8.56 | 35.87 | −12.98 | 40.29 | 110.2 | 93.6 | 126.9 | 90.3 | 130.2 |
| 8 hrs | 75.84 | 66.69 | 9.15 | 6.54 | −2.07 | 20.36 | −4.37 | 22.66 | 113.7 | 96.9 | 130.5 | 93.4 | 134.0 |
| 12 hrs | 31.88 | 30.97 | 0.91 | 3.42 | −4.85 | 6.68 | −6.00 | 7.82 | 102.9 | 84.3 | 121.6 | 80.6 | 125.3 |
| 24 hrs | 5.92 | 8.68 | −2.76 | 2.63 | −7.20 | 1.69 | −8.09 | 2.58 | 68.2 | 17.0 | 119.5 | 6.8 | 129.7 |
| 36 hrs | 1.58 | 1.56 | 0.02 | 1.14 | −1.96 | 2.00 | −2.38 | 2.41 | 101.1 | −26.1 | 228.2 | −52.7 | 254.8 |
| 48 hrs | 0.36 | 0.36 | 0.00 | 0.50 | −0.88 | 0.89 | −1.07 | 1.08 | 100.8 | −148.0 | 349.8 | −202.0 | 403.1 |

S = Searle tablets containing 50 mg hydrochlorothiazide and 75 mg triamterene
M = Maxzide tablets containing 50 mg hydrochlorothiazide and 75 mg triamterene
CI = Confidence interval including the preceding mean
S % = 100% × S/M
*Statistically different at p < 0.05 level.
~Statistically different at p < 0.1 level.

TABLE 6

URINE HCT ELIMINATION RATE
(mcg/hr after single 50 mg oral dose)

| Sample Time | Formulation S | Formulation M | Diff (S − M) Mean | St Dev | 90% CI | | 95% CI | | S % | 90% Ratio CI | | 95% Ratio CI | |
|---|---|---|---|---|---|---|---|---|---|---|---|---|---|
| −30 min | 15.38 | 0.00 | 15.38 | 11.39 | −4.94 | 35.69 | −9.42 | 40.17 | | | | | |
| +30 min | 798.46 | 668.04 | 130.42 | 134.97 | −96.49 | 357.33 | −141.35 | 402.19 | 119.5 | 85.6 | 153.5 | 78.8 | 160.2 |
| 1.5 hrs | 5516.01 | 5525.58 | −9.58 | 536.94 | −912.75 | 893.59 | −1091.5 | 1072.32 | 99.8 | 83.5 | 116.2 | 80.2 | 119.4 |
| 2.5 hrs | 5685.71 | 5161.70 | 524.01 | 448.03 | −290.59 | 1338.60 | −451.92 | 1499.94 | 110.2 | 94.4 | 125.9 | 91.2 | 129.1 |
| 3.5 hrs | 3878.18 | 3520.52 | 357.65 | 405.93 | −327.14 | 1042.45 | −463.39 | 1178.70 | 110.2 | 90.7 | 129.6 | 86.8 | 133.5 |
| 5 hrs | 2119.76 | 2143.46 | −23.70 | 242.27 | −429.52 | 382.13 | −509.21 | 461.82 | 98.9 | 80.0 | 117.8 | 76.2 | 121.5 |
| 7 hrs | 1271.85 | 1174.08 | 97.77 | 102.58 | −74.97 | 270.50 | −109.22 | 304.76 | 108.3 | 93.6 | 123.0 | 90.7 | 126.0 |
| 10 hrs | 742.72 | 744.93 | −2.21 | 78.38 | −133.46 | 129.04 | −159.22 | 154.79 | 99.7 | 82.1 | 117.3 | 78.6 | 120.8 |
| 18 hrs | 335.16 | 327.54 | 7.61 | 25.32 | −34.93 | 50.16 | −43.34 | 58.56 | 102.3 | 89.3 | 115.3 | 86.8 | 117.9 |
| 30 hrs | 163.96 | 176.69 | −12.72 | 13.02 | −34.63 | 9.18 | −38.97 | 13.52 | 92.8 | 80.4 | 105.2 | 77.9 | 107.7 |

S = Searle tablets containing 50 mg hydrochlorothiazide and 75 mg triamterene
M = Maxzide tablets containing 50 mg hydrochlorothiazide and 75 mg triamterene
CI = Confidence interval including the preceding mean
S % = 100% × S/M

TABLE 7

HCT CUMULATIVE ELIMINATION BY TIME
(Micrograms after single 50 mg oral dose)

| | Formulation | | Direct Effects | | | | | | Expressed as % of M | | | |
|---|---|---|---|---|---|---|---|---|---|---|---|---|
| Sample | | | | | Diff (S − M) | | | | | | | |
| Time | S | M | Mean | St Dev | 90% CI | | 95% CI | | S % | 90% Ratio CI | | 95% Ratio CI |
| 0 hr | 15.38 | 0.00 | 15.38 | 11.39 | −4.94 | 35.69 | −9.42 | 40.17 | | | | |
| 1 hr | 813.83 | 668.04 | 145.80 | 134.82 | −80.87 | 372.46 | −125.67 | 417.27 | 121.8 | 87.9 | 155.8 | 81.2 162.5 |
| 2 hrs | 6329.84 | 6193.62 | 136.22 | 620.82 | −907.52 | 1179.96 | −1113.8 | 1386.28 | 102.2 | 85.3 | 119.1 | 82.0 122.4 |
| 3 hrs | 12015.5 | 11355.3 | 660.23 | 918.50 | −885.57 | 2206.03 | −1191.7 | 2512.18 | 105.8 | 92.2 | 119.4 | 89.5 122.1 |
| 4 hrs | 15893.7 | 14875.8 | 1017.88 | 1120.44 | −872.27 | 2908.03 | −1248.3 | 3284.10 | 106.8 | 94.1 | 119.5 | 91.6 122.1 |
| 6 hrs | 20133.2 | 19162.8 | 970.49 | 1405.36 | −1401.9 | 3342.91 | −1874.5 | 3815.48 | 105.1 | 92.7 | 117.4 | 90.2 119.9 |
| 8 hrs | 22676.9 | 21510.9 | 1166.03 | 1532.82 | −1421.6 | 3753.62 | −1937 | 4269.05 | 105.4 | 93.4 | 117.4 | 91.0 119.8 |
| 12 hrs | 25647.8 | 24490.6 | 1157.18 | 1746.73 | −1787.6 | 4101.98 | −2372.7 | 4687.07 | 104.7 | 92.7 | 116.7 | 90.3 119.1 |
| 24 hrs | 29669.7 | 28421.1 | 1248.53 | 1967.79 | −2066.9 | 4564.00 | −2725 | 5222.06 | 104.4 | 92.7 | 116.1 | 90.4 118.4 |
| 36 hrs | 31637.2 | 30541.4 | 1095.84 | 2054.23 | −2365.3 | 4556.94 | −3052.2 | 5243.91 | 103.6 | 92.3 | 114.9 | 90.0 117.2 |

S = Searle tablets containing 50 mg hydrochlorothiazide and 75 mg triamterene
M = Maxzide tablets containing 50 mg hydrochlorothiazide and 75 mg triamterene
CI = Confidence interval including the preceding mean
S % = 100% × S/M

TABLE 8

BIOAVAILABILITY COMPARISON

| | Formulation | | Direct Effects | | | | | | Expressed as % of M | | | |
|---|---|---|---|---|---|---|---|---|---|---|---|---|
| | | | | | Diff (S − M) | | | | | | | |
| | S | M | Mean | St. Dev | 90% CI | | 95% CI | | S % | 90% CI | | 95% CI |
| TRIAMTERENE | | | | | | | | | | | | |
| AUC (hr.ng/ml) | 480.04 | 398.98 | 81.06 | 42.77 | 9.31 | 152.81~ | −4.82 | 166.94 | 120.3 | 102.3 | 138.3~ | 98.8 141.8 |
| Cmax (ng/ml) | 144.58 | 118.62 | 25.96 | 13.31 | 3.62 | 48.29~ | −0.77 | 52.69 | 121.9 | 103.1 | 140.7~ | 99.3 144.4 |
| Tmax (hour) | 0.93 | 1.02 | −0.09 | 0.11 | −0.27 | 0.09 | −0.31 | 0.12 | 91.0 | 73.4 | 108.5 | 69.9 112.0 |
| Beta (/hour) | 0.14 | 0.13 | 0.01 | 0.01 | −0.01 | 0.02 | −0.01 | 0.03 | 104.9 | 91.2 | 118.5 | 88.5 121.2 |
| T-half (hour) | 6.45 | 7.13 | −0.69 | 1.36 | −3.02 | 1.65 | −3.50 | 2.13 | 90.4 | 57.6 | 123.2 | 50.9 129.9 |
| TRM-O—SO4 | | | | | | | | | | | | |
| AUC (hr.ng/ml) | 3814.62 | 3423.08 | 391.54 | 160.41 | 122.66 | 660.43~ | 69.79 | 713.30* | 111.4 | 103.6 | 119.3~ | 102.0 120.8* |
| Cmax (ng/ml) | 1252.91 | 1117.20 | 135.72 | 83.53 | −4.78 | 276.22 | −32.59 | 304.03 | 112.1 | 99.6 | 124.7 | 97.1 127.2 |
| Tmax (hour) | 1.10 | 1.15 | −0.05 | 0.08 | −0.19 | 0.09 | −0.22 | 0.12 | 95.5 | 83.3 | 107.7 | 80.9 110.2 |
| Beta (/hour) | 0.10 | 0.10 | 0.01 | 0.01 | −0.01 | 0.02 | −0.02 | 0.03 | 105.8 | 88.0 | 123.7 | 84.5 127.1 |
| T-half (hour) | 8.77 | 9.92 | −1.15 | 1.46 | −3.63 | 1.32 | −4.12 | 1.82 | 88.4 | 63.4 | 113.3 | 58.4 118.3 |
| HYDROCHLOROTHIAZIDE | | | | | | | | | | | | |
| AUC (mcg) | 32165.0 | 30874.9 | 1290.17 | 2126.85 | −2293.3 | 4873.62 | −3004.5 | 5584.87 | 104.2 | 92.6 | 115.8 | 90.3 118.1 |
| Rmax (mcg/hr) | 6444.71 | 6325.57 | 119.15 | 508.99 | −740.09 | 978.38 | −911.24 | 1149.54 | 101.9 | 88.3 | 115.5 | 85.6 118.2 |
| Tmax (hour) | 2.16 | 2.10 | 0.06 | 0.16 | −0.21 | 0.33 | −0.27 | 0.39 | 102.8 | 89.7 | 115.9 | 87.2 118.4 |
| Beta (/hour) | 0.04 | 0.03 | 0.00 | 0.00 | 0.00 | 0.01 | −0.00 | 0.01 | 108.6 | 100.2 | 117.0~ | 98.6 118.6 |
| T-half (hour) | 19.52 | 22.00 | −2.48 | 1.38 | −4.84 | −0.12~ | −5.32 | 0.36 | 88.7 | 78.0 | 99.5~ | 75.8 101.7 |
| Elim 36 hour (%) | 63.3 | 61.1 | 2.2 | 4.1 | −2365.3 | 4556.94 | −2.0 | 10.5 | 103.6 | 92.3 | 114.9 | 90.0 117.2 |

S = Searle tablets containing 50 mg hydrochlorothiazide and 75 mg triamterene
M = Maxzide tablets containing 50 mg hydrochlorothiazide and 75 mg triamterene
CI = Confidence Interval including the preceding mean
Elim 36 Hour = Cumulative Elimination at 36 hours
~Statistically different at p < 0.1 level.
*Statistically different at p < 0.05 level.

What is claimed is:

1. A process for producing a pharmaceutically active composition having combined diuretic, antihypokalemic and antihypertensive activity comprising the steps of
   (a) blending finely divided particles of a triamterene-active pteridine ingredient, a finely-divided hydrochlorothiazide-active benzothiadiazide and pharmaceutically acceptable inert ingredients to form a homogeneous mixture;
   (b) adding to said homogeneous mixture a granulation liquid which is prepared by dispersing/dissolving a suitable binder and an acid component in a solvent to form a wet mass;
   (c) milling of said mass to form granules; and
   (d) blending the resulting granules with additional pharmaceutically acceptable inert ingredients wherein the weight ratio of said triamterene active ingredient to said hydrochlorothiazide active ingredient in the resulting composition is sufficient to control the hypokalemic effect induced by hydrochlorothiazide.

2. A process for producing a phgarmaceutically active composition having combined diuretic, antihypokalemic and antihypertensive activity comprising the steps of
   (a) blending finely divided particles of triamterene, finely divided particles of hydrochlorothiazide and a wicking, binding, disintegration agent to form a homogeneous mixture;
   (b) adding to said homogeneous mixture a granulation liquid which is prepared by dispersing/dissolving a suitable binder and malic acid in the presence of water to form a wet mass;

(c) milling of said wet mass to form granules;

(d) drying of the wet granules;

(e) sizing of the dried granules; and blending of said sized granules with a lubricant agent and a disintegrant agent so that in the resulting composition the weight ratio of said triamterene to said hydrochlorothiazide is sufficient to control the hypokalemic effect induced by hydrochlorothiazide.

3. The process according to claim 2 wherein the amount of malic acid is about 5 to 45 percent on a triamterene weight basis.

4. The process according to claim 2 wherein the amount of water is about 50 to 650 percent on a triamterene weight basis.

5. A process according to claim 2 wherein the traimterene:hydrochlorothiazide weight ratio is from 1.25 to 2.00:1.

6. A process according to claim 5 wherein the traimterene: hydrochlorothiazide weight ratio is about 1.5:1.

7. A method of treating hypertension comprising administering a solid antihypertensive diuretic medication wherein said solid medication is composed essentially of hydrochlorothiazide and triamterene and wherein said solid medication is formed by blending finely divided particles of triamterene, finely divided particles of hydrochlorothiazide and a wicking, binding, disintegration agent to form a homogeneous mixture, adding to said homogeneous mixture a granulation liquid which is prepared by dispersing/dissolving a suitable binder and malic acid in the presence of water to form a wet mass, milling of said wet mass to form granules, drying of the wet granules, sizing of the dried granules, and blending of said sized granules with a lubricant agent and a disintegrant agent so that in the resulting composition the weight ratio of said triamterene to said hydrochlorothiazide is sufficient to control the hypokalemic effect induced by hydrochlorothiazide.

8. A method according to claim 7 wherein said solid medication is formulated as a tablet by compression.

9. A method according to claim 7 wherein said solid medication is formulated as a capsule.

10. A method according to claim 7 wherein the triamterene:hydrochlorothiazide weight ratio is from 1.25 to 2.00:1.

11. A method according to claim 10 wherein the triamterene: hydrochlorothiazide weight ratio is about 1.5:1.

12. A pharmaceutical combination composition having combined diuretic, antihypokalemic and antihypertensive activity wherein said composition is prepared by blending finely divided particles of triamterene, finely divided particles of hydrochlorothiazide and a wicking, binding, disintegration agent to form a homogeneous mixture, adding to said homogeneous mixture a granulation liquid which is prepared by dispersing/dissolving a suitable binder and malic acid in the presence of water to form a wet mass, milling of said wet mass to form granules, drying of the wet granules, sizing of the dried granules, and blending of said sized granules with a lubricant agent and a disintegrant agent so that in the resulting composition the weight ratio of said triamterene to said hycrochlorothiazide is sufficient to control the hypokalemic effect induced by hydrochlorothiazide.

13. A composition according to claim 12 wherein the triamterene:hydrochlorothiazide weight ratio is from 1.25 to 2.00:1.

14. A composition according to claim 13 wherein the triamterene:hydrochlorothiazide weight ratio is about 1.5:1.

* * * * *

UNITED STATES PATENT AND TRADEMARK OFFICE
CERTIFICATE OF CORRECTION

PATENT NO. : 4,804,540

DATED : Feb. 14, 1989

INVENTOR(S) : Nugent, et al.

It is certified that error appears in the above-identified patent and that said Letters Patent is hereby corrected as shown below:

Column 10, line 39, reading "$-SO_2$" should read -- $-SO_4$ --.

Columns 11-12, Table 4, the second line under the heading "M", reading "101.12" should read -- 102.12 --.

Columns 11-12, Table 4, the seventh line under the heading "S", reading "65.15" should read -- 65.16 --.

Columns 11-12, Table 4, the seventh line under the heading "90% CI", the right-hand column, reading "22.14" should read -- 22.15 --.

Columns 11-12, Table 6, the fourth line under the heading "St Dev", reading "448.03" should read -- 484.03 --.

Column 13, line 66, reading "said mass" should read -- said wet mass --.

Signed and Sealed this

Fourth Day of September, 1990

Attest:

HARRY F. MANBECK, JR.

*Attesting Officer*  *Commissioner of Patents and Trademarks*